United States Patent [19]

Mitch

[11] Patent Number: 5,834,458
[45] Date of Patent: Nov. 10, 1998

[54] HETEROCYCLIC COMPOUNDS AND THEIR USE

[75] Inventor: Charles H. Mitch, Columbus, Ind.

[73] Assignee: Eli Lilly and Company, Indianapolis, Ind.

[21] Appl. No.: 723,459

[22] Filed: Oct. 9, 1996

[51] Int. Cl.$^6$ ................................................. A61K 31/545
[52] U.S. Cl. .................. 514/200; 424/78.08; 424/78.36; 514/183; 514/203; 514/210; 514/772.3
[58] Field of Search ............................. 424/78.08, 78.36; 514/183, 200, 203, 210, 772.3

[56] References Cited

U.S. PATENT DOCUMENTS

| | | | |
|---|---|---|---|
| 5,098,888 | 3/1992 | Vincent et al. | 514/18 |
| 5,391,761 | 2/1995 | Laborit et al. | 548/452 |
| 5,571,819 | 11/1996 | Sabb et al. | 514/303 |
| 5,629,322 | 5/1997 | Guthikonda et al. | 514/313 |
| 5,641,784 | 6/1997 | Kufner-Muhl et al. | 514/263 |

FOREIGN PATENT DOCUMENTS

| | | |
|---|---|---|
| 0 239 309 | 9/1987 | European Pat. Off. . |
| 0 307 142 | 3/1989 | European Pat. Off. . |
| 0 327 155 | 9/1989 | European Pat. Off. . |
| 0 412 798 | 2/1991 | European Pat. Off. . |
| 0 492 903 | 7/1992 | European Pat. Off. . |
| WO 92/03433 | 3/1992 | WIPO . |
| WO 93/14089 | 7/1993 | WIPO . |

*Primary Examiner*—Samuel A. Acquah
*Attorney, Agent, or Firm*—Arleen Palmberg; MaCharri Vorndran-Jones; David E. Boone

[57] ABSTRACT

The present invention relates to therapeutically active heterocyclic compounds and to pharmaceutical compositions comprising the compounds. The novel compounds are useful in treating diseases in the central nervous system caused by malfunctioning of the muscarinic cholinergic system.

16 Claims, No Drawings

HETEROCYCLIC COMPOUNDS AND THEIR USE

FIELD OF THE INVENTION

The present invention relates to therapeutically active azabicyclic compounds and to compositions for pharmaceutical or veterinary use comprising the compounds and a carrier therefore. The novel compounds are useful as stimulants of the cognitive function of the forebrain and hippocampus of mammals and especially in the treatment of Alzheimer's disease.

BACKGROUND OF THE INVENTION

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic receptors in the forebrain and hippocampus still exist. Therefore, cholinergic agonists are useful in the treatment of Alzheimer's disease, in halting its progression, and in improving the cognitive functions of elderly people.

The compounds of this invention are also useful analgesic agents and therfore useful in the treatment of severe painful conditions.

Furthermore, the compounds of this invention are useful in the treatment of glaucoma, psychosis, mania, bipolar disorder, schizophrenia or schizophreniform conditions, depression, bladder dysfunctions, anxiety, sleeping disorders, epilepsy, and gastrointestinal motility disorders.

SUMMARY OF THE INVENTION

It is an object of the invention to provide new muscarinic cholinergic compounds.

The novel compounds of the invention are heterocyclic compounds having the Formula I

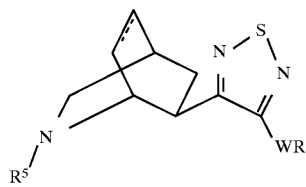

wherein

W is oxygen or sulphur;

R is selected from the group consisting of hydrogen, $R^4$, G, $C_{3-10}$-cycloalkyl, $C_{4-12}$-(cycloalkylalkyl), aryl, aryl $(C_{1-3})$alkyl, $C_1$–$C_6$ alkylheterocycle and heterocycle, each of which is optionally substituted with one or more independently selected from the group consisting of halogen(s), —$CF_3$, —CN, $C_{1-15}$-alkyl, $C_{2-5}$-alkenyl, $C_{2-5}$-alkynyl, and $C_{1-10}$-alkoxy;

$R^5$ is hydrogen, $R^4$, G, $C_{3-10}$-cycloalkyl, $C_{4-12}$-(cycloalkylalkyl), aryl, each of which is optionally substituted with one or more independently selected from the group consisting of halogen(s), —$CF_3$, —CN, $C_{1-15}$-alkyl, $C_{2-5}$-alkenyl, $C_{2-5}$-alkynyl, and $C_{1-10}$-alkoxy;

$R^4$ is selected from the group consisting of $C_{1-15}$-alkyl, substituted $C_{1-15}$-alkyl, $C_{2-15}$-alkenyl, and $C_{2-15}$-alkynyl;

G is selected from one of the following azacyclic or azabicyclic ring systems:

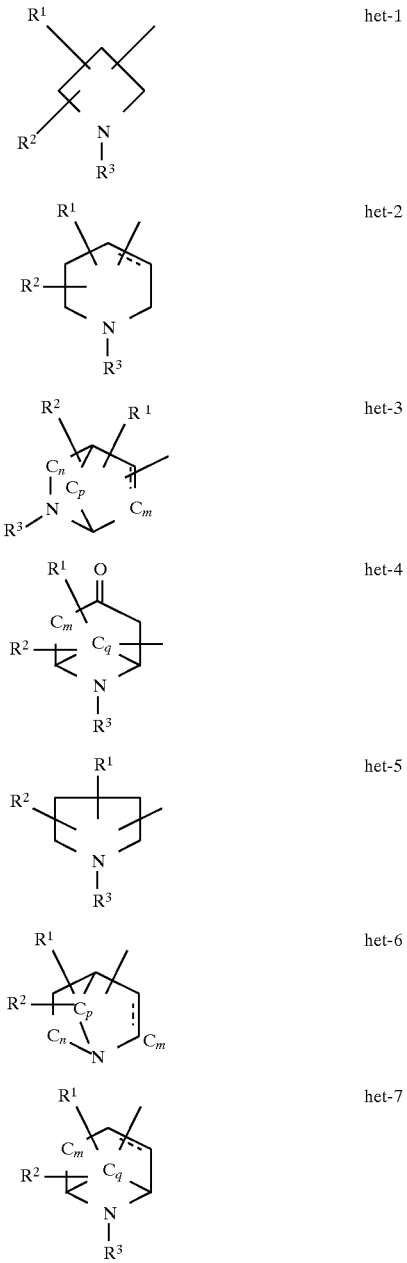

or G can optionally be substituted $C_3$–$C_8$cycloalkyl or optionally substituted $C_{1-6}$-alkyl wherein the substitution is —$NR^6R^7$;

$R^6$ and $R^7$ independently are hydrogen, $C_{1-6}$-alkyl; or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —$COR^{6'}$, $CH_2$—OH, halogen, —$NH_2$, carboxy, or phenyl;

$R^3$ is hydrogen, $C_{1-5}$-alkyl, $C_{2-5}$-alkenyl or $C_{2-5}$-alkynyl;

$R^{6'}$ is hydrogen, $C_{1-6}$-alkyl;

n is 0, 1 or 2;

m is 0, 1 or 2;

p is 0, 1 or 2;

q is 1 or 2;

r is 0, 1 or 2;

⋯⋯ is a single or double bond; or a pharmaceutically acceptable salt or solvate thereof.

The invention further provides a formulation comprising a compound of Formula 1 and one or more pharmaceutically acceptable diluents, carriers, or excipients therefor.

The invention provides a method for treating a condition associated with a malfunction of the cholinergic muscarinic receptor system. Such conditions which may be treated using a compound of this invention include, but are not limited to Alzheimer's Disease, cognitive dysfunction, severely painful conditions, glaucoma, psychosis, schizophrenia, bladder dysfunction, anxiety, sleep disorders, and other such conditions associated with the modulation of a muscarinic receptor.

It is to be understood that the invention extends to each of the stereoisomeric forms of the compounds of the present invention as well as the pure diastereomeric, pure enatiomeric, and racemic forms of the compounds of Formula I.

DETAILED DESCRIPTION

As used herein the term "treating" includes prophylaxis of a physical and/or mental condition or amelioration or elimination of the developed physical and/or mental condition once it has been established or alleviation of the characteristic symptoms of such condition.

As used herein with reference to the G substituent, the azabicyclic moiety can be attached at any carbon atom of the azacyclic or azabicyclic ring. Further, $R^1$ and $R^2$ of the G substituent may be present at any position, including the point of attachment of the azabicyclic moiety.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

As used herein with reference to the G substituent, the numbering shall be as follows:

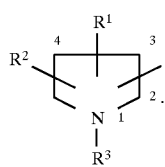

As used herein the term α shall refer to a position on the G substituent which is one position away from the N atom of the G substituent. For example, in the following illustration (1E), both positions 2 and 6 are considered α. The term γ shall refer to the position on the G substituent which is opposite the N atom. For example, in the illustration (1E), position 4 is considered γ. Likewise, β shall refer to the 3 and 5 position in the illustration.

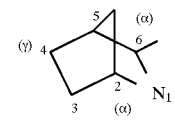

As used herein with reference to the G substituent, the phrase "$R^6$ and $R^7$ together with the nitrogen atom optionally form a 4- to 6-member ring" means that $R^6$ and $R^7$ are each independently hydrogen, $C_1$–$C_6$ alkyl; the $R^6$ and $R^7$ groups may optionally join to form a 4- to 6-member ring including the nitrogen. For example, optionally joined groups include, but not limited to:

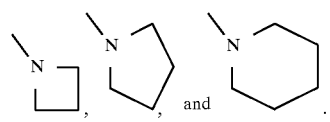

As used herein the phrase "interacting with a muscarinic cholinergic receptor" shall include compounds which block muscarinic cholinergic receptors or modulate such receptors. Likewise, the term "interacting with a nicotinic cholinergic receptor" shall include compounds which block or modulate the receptor. The phrase shall include the effect observed when compounds act as agonists, partial agonists and/or antagonists at a cholinergic receptor.

As used herein, the term "alkoxide metal" means a metal suitable for alkoxide formation. Such alkoxide metals include, but are not limited to, $Li^+$, $K^+$, $Na^+$, $Cs^+$, and $Ca^{++}$. Especially preferred alkoxide metals include $Li^+$, $K^+$, and $Na^+$.

As used herein, the term "halogen" means Cl, Br, F, and I. Especially preferred halogens include Cl, Br, and I.

The terms "$C_1$–$C_{n'}$ alkyl" wherein n' can be from 2 through 15, as used herein, represent a branched or linear alkyl group having from one to the specified number of carbon atoms. Typical $C_1$–$C_6$ alkyl groups include methyl, ethyl, n-propyl, iso-propyl, butyl, iso-butyl, sec-butyl, tert-butyl, pentyl, hexyl and the like.

The term "substituted($C_5$–$C_{n'}$) alkyl" refers to an alkyl group as described supra wherein the alkyl group may be substituted with from one to four substituents independently selected from the group consisting of hydrogen, aryl, substituted aryl, $C_1$–$C_6$ alkyl, $NO_2$, halogen, halogen($C_1$–$C_6$) alkyl, halogen($C_2$–$C_6$)alkenyl, $C_2$–$C_6$ alkenyl, $CO_2R^{20}$, ($C_1$–$C_6$ alkyl) amino, —$SR^{20}$, and $OR^{20}$; wherein $R^{20}$ is selected from the group consisting of $C_{1-15}$-alkyl, $C_{2-15}$-alkenyl, aryl, substituted aryl, and $C_{2-15}$-alkynyl.

The terms "$C_2$–$C_{n'}$ alkenyl" wherein n' can be from 3 through 10, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=CHCH$_2$CH$_3$), hexenyl, pentenyl, and the like.

The term "$C_2$–$C_5$ alkynyl" refers to an unsaturated branched or linear group having from 2 to 5 carbon atoms and at least one triple bond. Examples of such groups include, but are not limited to, 1-propynyl, 2-propynyl, 1-butynyl, 2-butynyl, 1-pentynyl, and the like.

The terms "halogen($C_1$–$C_6$)alkyl" and "halogen($C_2$–$C_6$) alkenyl" refer to alkyl or alkenyl substituents having one or more independently selected halogen atoms attached at one or more available carbon atoms. These terms include, but are not limited to, chloromethyl, 1-bromoethyl, 2-bromoethyl, 1,1,1-trifluoroethyl, 1,1,2-trifluoroethyl, 1,2,2-trifluoroethyl, 2,2,2-trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, 1-chloroethylenyl, 2-chloroethylenyl, 5-fluoro-3-pentenyl, 3-chloro-2-bromo-5-hexenyl, 3-chloro-2-bromobutyl, trichloromethyl, 1,1-dichloroethyl, 1,2-dichloroethyl, 2,2-dichloroethyl, 1,4-dichlorobutyl, 3-bromopentyl, 1,3-dichlorobutyl, 1,1-dichloropropyl, and the like.

The term "$C_2$–$C_{10}$ alkanoyl" represents a group of the formula C(O) ($C_1$–$C_9$) alkyl. Typical $C_2$–$C_{10}$alkanoyl groups include acetyl, propanoyl, butanoyl, and the like.

The term "($C_1$–$C_6$ alkyl) amino" refers to a monoalkylamino group. Examples of such groups are methylamino, ethylamino, iso-propylamino, n-propylamino, (n-propyl) amino, (iso-propyl)amino, n-propylamino, t-butylamino, and the like.

The term "$C_3$–$C_n$ cycloalkyl", wherein n=4–8, represents cyclopropyl, cyclobutyl, cyclopentyl, cyclohexyl, cycloheptyl, and cyclooctyl.

The term "substituted($C_5$–$C_{n'}$) cycloalkyl", refers to a cycloalkyl group as described supra wherein the cycloalkyl group may be substituted with from one to four substituents independently selected from the group consisting of hydrogen, $C_1$–$C_6$ alkyl, $NO_2$, halogen, halogen($C_1$–$C_6$) alkyl, halogen($C_2$–$C_6$)alkenyl, $C_2$–$C_6$ alkenyl, $CO_2R^{20}$, ($C_1$–$C_6$ alkyl) amino, —$SR^{20}$, and $OR^{20}$; wherein $R^{20}$ is selected from the group consisting of $C_{1-15}$-alkyl, $C_{2-15}$-alkenyl, and $C_{2-15}$-alkynyl.

The term "$C_3$–$C_8$ cycloalkyl-($C_1$–$C_3$)alkyl" represents an alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms. Such groups include, but are not limited to, cyclohexyl-1,3-dienyl, cyclohexenyl, cyclopentenyl, cycloheptenyl, cyclooctenyl, cyclohexyl-1,4-dienyl, cycloheptyl-1,4-dienyl, cyclooctyl-1,3,5-trienyl and the like.

The term "substituted ($C_5$–$C_8$) cycloalkenyl" refers to a cycloalkenyl group as described supra. wherein the cycloalkenyl group may be substituted with from one to four substituents independently selected from the group consisting of hydrogen, $C_1$–$C_6$ alkyl, $NO_2$, halogen, halogen ($C_1$–$C_6$)alkyl, halogen($C_2$–$C_6$)alkenyl, $C_2$–$C_6$ alkenyl, $COR^{20}$, $C_2$–$C_{10}$ alkanoyl, $C_7$–$C_{16}$ arylalkyl, $CO_2R^{20}$, ($C_1$–$C_6$ alkyl) amino, —$SR^{20}$, and —$OR^{20}$. Wherein $R^{20}$ is selected from the group consisting of $C_{1-15}$-alkyl, $C_{2-15}$-alkenyl, $C_{2-15}$-alkynyl.

The term "$C_5$–$C_8$ cycloalkenyl-($C_1$–$C_3$)alkyl" represents a $C_1$–$C_3$ alkyl group substituted at a terminal carbon with a $C_5$–$C_8$ cycloalkenyl group.

As used herein, the phrase "heterocycle" means a group containing from one to four N, O or S atom(s) or a combination thereof, which heterocyclic group is optionally substituted at carbon or nitrogen atom(s) with $C_{1-6}$-alkyl, —$CF_3$, phenyl, benzyl or thienyl, or a carbon atom in the heterocyclic group together with an oxygen atom form a carbonyl group, or which heterocyclic group is optionally fused with a phenyl group. The phrase "heterocycle" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having 3-heteroatoms; 6-membered heterocycles with one heteroatom (e.g. pyridine, quinoline, isoquinoline, phenanthrine, 5,6-cycloheptenopyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-member heterocycles with four heteroatoms. Particularly preferred are thiophenes, pyridines, and furans.

The term "$C_1$–$C_6$ alkylheterocycle" means an alkyl group attached to the nucleus molecule (for example, but not limited to, at the W substituent) and a heterocycle attached at the distal end of the alkyl group. One example is W—$CH_2$-thiophene; however, the term is in no way limited to this single embodiment.

The term "heteroaryl" refers to a group which is a 5 or 6 membered heterocycle containing one to four N, O, or S atoms or a combination thereof.

As used herein the term "carboxy" refers to a substituent having the common meaning understood by the skilled artisan, wherein the point of attachment may be through the carbon or oxygen atom of the group.

As used herein the term "aryl" means an organic radical derived from an aromatic hydrocarbon by the removal of one atom; e.g., phenyl or naphthyl. Most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The term "aryl($C_1$–$C_3$) alkyl", refers to any aryl group which is attached to the parent moiety via the alkyl group. "Substituted aryl" refers to an aryl group which may be substituted with from one to three substituents selected from the group consisting of halogen(s), —$CF_3$, —CN, $C_{1-15}$-alkyl, $C_{2-5}$-alkenyl, $C_{2-5}$-alkynyl, and $C_{1-10}$-alkoxy.

The compounds of this invention can be prepared using the following methods:

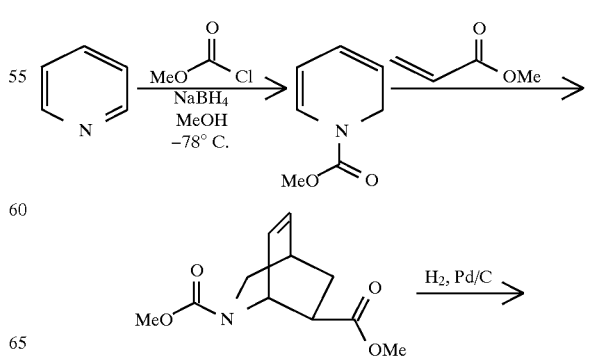

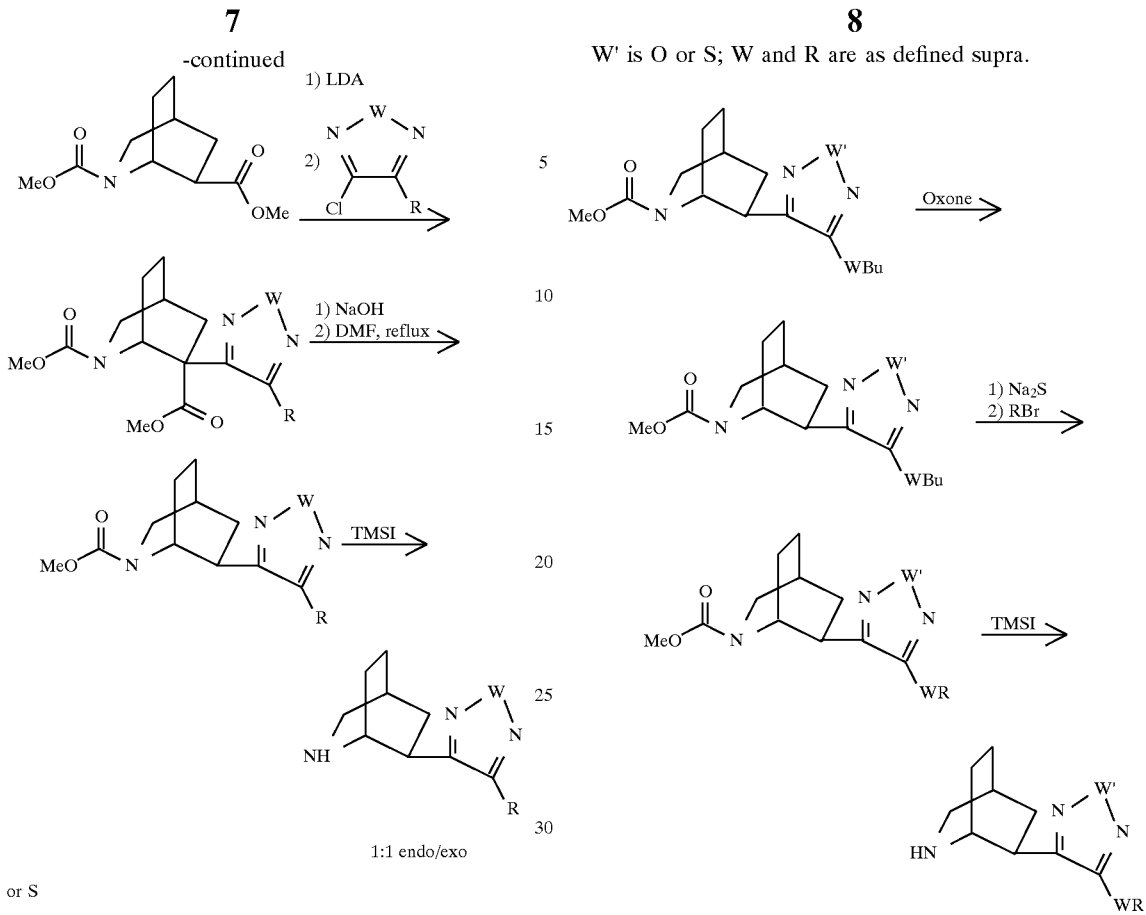
W is O or S
R is as defined supra.
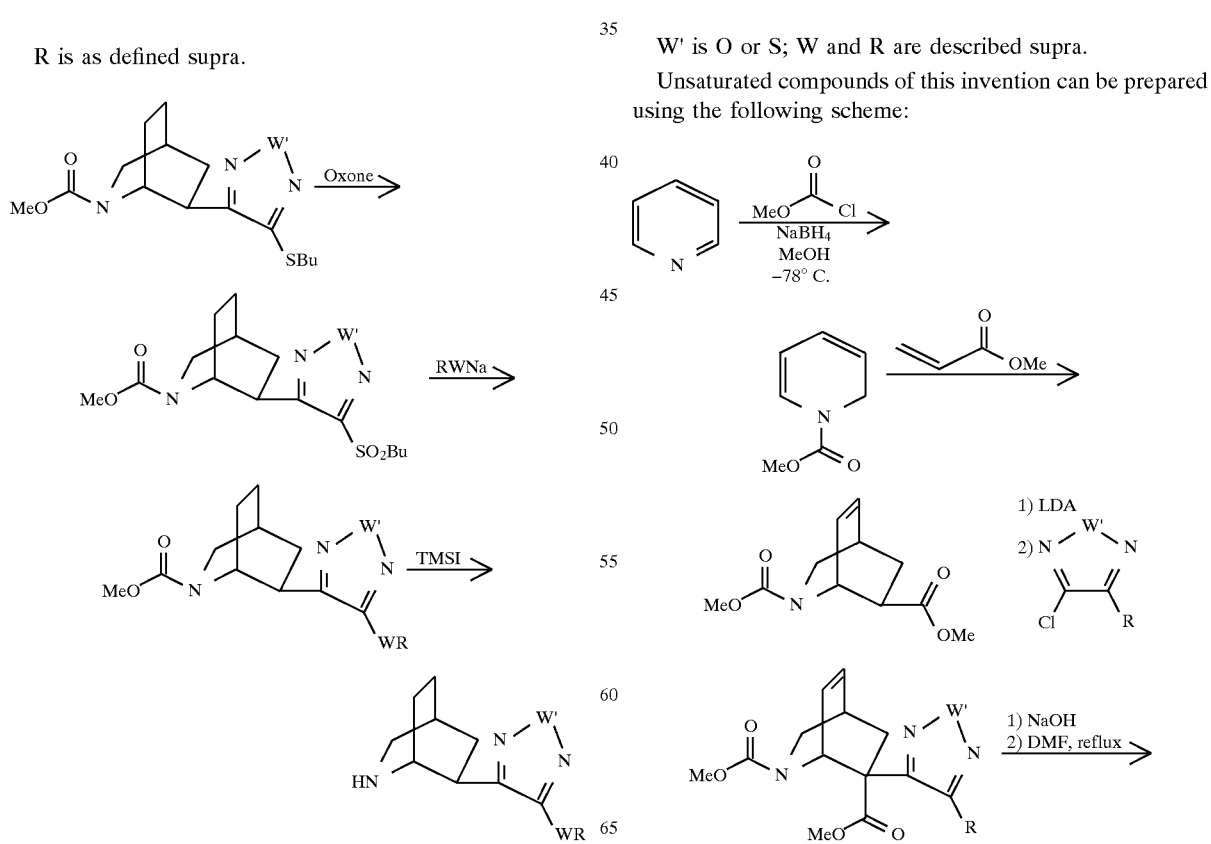
W' is O or S; W and R are as defined supra.
W' is O or S; W and R are described supra.
Unsaturated compounds of this invention can be prepared using the following scheme:

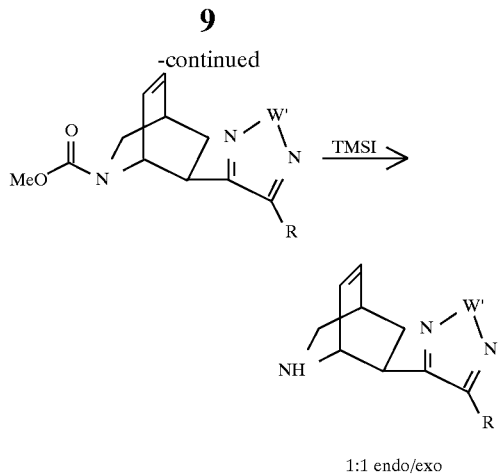

1:1 endo/exo

R and W are defined supra.

The compounds of this invention can be prepared as described supra. and by using the chemical processes illustrated in the Schemes. The starting materials for the illustrated process are commercially available or may be prepared using methods known to the skilled artisan.

As used herein the term "malfunctioning of the muscarinic cholinergic system" shall have the meaning accepted by the skilled artisan. Likewise, the term "malfunctioning of the nicotinic cholinergic system" shall have the art recognized meaning. For example the term shall refer to, but is not in any way limited to, conditions such as glaucoma, psychosis, schizophrenia or schizophreniform conditions, depression, sleeping disorders, epilepsy, and gastrointestinal motility disorders. Other such conditions include Alzheimer's Disease and incontinence.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-oxo labels muscarinic receptor in the CNS (with a preference for agonist domains of the receptors). Three different sites are labeled by $^3$H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0°–4° C. unless otherwise indicated. Fresh cortex (0.1–1 g) from male Wistar rats (150–250 g) is homogenized for 5–10 s in 10 mL 20 nM Hepes pH: 7.4, with an Ultra-Turrax homogenizer. The homogenizer is rinsed with 10 mL of buffer and the combined suspension centrifuged for 15 min. at 40,000×g. The pellet is washed three times with buffer. In each step the pellet is homogenized as before in 2×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 25 μL of test solution and 25 μL of $^3$H-Oxotremorine (1.0 nM, final concentration) mixed and incubated for 30 min. at 25° C. Non-specific binding is determined in triplicate using arecoline (1 μg/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of $IC_{50}$. The test value will be given as $IC_{50}$ (the concentration (nM) of the test substance which inhibits the specific binding of $^3$H-oxo by 50%). $IC_{50}$=(applied test substance concentration) $x(C_x/C_o-C_x)$nM where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$HPRZ (pirenzepine, [N-methyl-$^3$H]) binding to rat cerebral cortex membranes.

Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0°–4° C. unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2×10 mL of buffer and the combined suspension centrifuged for 15 min. at 40,000×g. The pellet is washed three times with buffer. In each step the pellet is homogenized as before in 3×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 20 μL of test solution and 25 μL of $^3$HPRZ (1.0 nM, final conc.), mixed and incubated for 60 min. at 20° C. Non-specific binding is determined in triplicate using atropine (1.0 μg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of $IC_{50}$.

The test value will be given as $IC_{50}$ (the concentration (nM) of the test substance which inhibits the specific binding of $^3$HPRZ by 50%). $IC_{50}$=(applied test substance concentration) $x(C_x/C_o-C_x)$nM where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound | $^3$H-Oxo-M $IC_{50}$, nM | $^3$HPRZ $IC_{50}$, nM |
|---|---|---|
| 4 | 4.2 | 17 |
| 30 | 5.9 | 15 |
| 7 | 4.8 | 21 |
| 19 | 18 | 128 |
| 11 | 4.1 | 13 |
| 9 | 2 | 2.7 |

TABLE 1-continued

| Compound | $^3$H-Oxo-M IC$_{50}$, nM | $^3$HPRZ IC$_{50}$, nM |
|---|---|---|
| 15 | 3.4 | 5 |
| 27 | 3 | 2.3 |
| 20 | 4.8 | 5.5 |
| 18 | 17 | 13 |
| 23 | 26 | 36 |
| 25 | 5.4 | 6.2 |
| 13 | 263 | 172 |
| 5 | 143 | 139 |
| 31 | 161 | 80 |
| 8 | 277 | 58 |
| 14 | 685 | 365 |
| 16 | 83 | 45 |
| 28 | 86 | 62 |
| 17 | 612 | 170 |
| 24 | 60 | 91 |
| 26 | 31 | 20 |
| 22 | 680 | 444 |
| 33 | 208 | 273 |
| 32 | 335 | 244 |

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated, the body weight of the subject to be treated, and the preference and experience of the physician or prescribing caregiver in charge.

The route of administration may be any route, which effectively transports the active compound to the appropriate or desired site of action, such as oral or parenteral e.g. rectal, transdermal, depot, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

In order to more fully illustrate the operation of this invention, the following formulation examples are provided. The examples are illustrative only, and are not intended to limit the scope of the invention in any way.

FORMULATION 1

A typical tablet, appropriate for use in this method, may be prepared using conventional techniques and may contain:

| | Amount per Tablet | Concentration by Weight (%) |
|---|---|---|
| Endo-2-aza-6-(4-hexylthio)-1,2,5-thiadiaz-3-yl)-bicyclo-[2.2.2.]octane | 5.0 mg | 4.7 |
| Lactosum | 67.8 mg Ph. Eur. | 64.2 |
| Avicel ® | 31.4 mg | 29.8 |
| Amberlite ® | 1.0 mg | 1.0 |
| magnesium stearate | 0.25 mg Ph. Eur. | 0.3 |
| | 105.45 mg | 100 |

FORMULATION 2

Hard gelatin capsules are prepared using the following ingredients:

| | Amount per Tablet | Concentration by Weight (%) |
|---|---|---|
| Exo-2-aza-6-(4,4,4-trifluorobutyl)thio)-1,2,5-thiadiaz-3-yl)-bicyclo-[2.2.2.]octane | 0.1 mg | 0.05 |
| starch dried | 200 mg | 95.2 |
| magnesium stearate | 10 mg | 4.8 |
| | 210.1 mg | 100 |

The above ingredients are mixed and filled into hard gelatin capsules in 210.1 mg quantities.

FORMULATION 3

Suspensions each containing 1 mg of medicament per 5 mL dose are as follows:

|  | Amount per 5 mL of suspension |
| --- | --- |
| Exo-2-aza-6-(4-fluoroethyl)thio)-1,2,5-thiadiaz-3-yl)-bicyclo[2.2.2]octane | 1 mg |
| sodium carboxymethyl cellulose | 50 mg |
| syrup | 1.25 mL |
| benzoic acid solution | 0.10 mL |
| flavor | q.v. |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The compounds of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be adminstered as a feed additive or in bulk form.

The compounds of the present invention have useful muscarinic receptor activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of formula I are:

A) W is S;

B) r is 1 or 2;

C) the bicyclic ring is saturated;

D) $R^5$ is H;

E) R is aryl($C_1$–$C_3$)alkyl;

F) R is alkyl-substituted phenyl wherein the phenyl substituents are selected from CN, $CF_3$, and F;

G) R is alkyl- substituted thiazole wherein the thiazole substituents are selected from CN, $CF_3$, and F; and H) $R^4$ is substituted $C_1$–$C_3$ alkyl wherein the alkyl is substituted with from one to four substituents independently selected from the group consisting of hydrogen, $C_1$–$C_6$ alkyl, halogen, halogen ($C_1$–$C_6$) alkyl, halogen ($C_2$–$C_6$)alkenyl, $C_2$–$C_6$ alkenyl, ($C_1$–$C_6$ alkyl) amino, aryl, substituted aryl, —$SR^{20}$, and $OR^{20}$; wherein $R^{20}$ is selected from the group consisting of $C_{1-15}$-alkyl, $C_{2-15}$-alkenyl, $C_{2-15}$-alkynyl, aryl, and substituted aryl.

Further, especially preferred G groups include the following heterocycles:

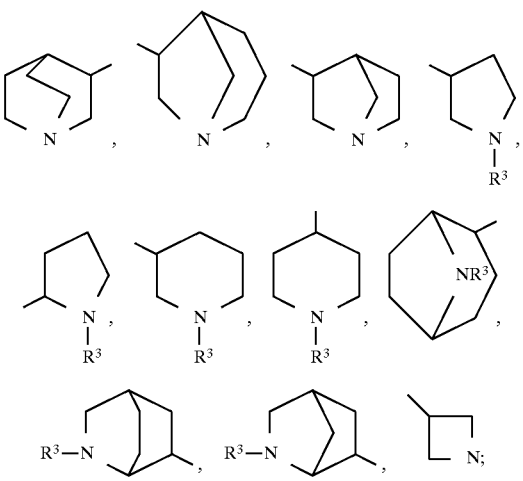

wherein the point of attachment to the —($CH_2$)$_r$—W— group is as indicated

The invention will now be described in further detail with reference to the following examples. The examples are provided for illustrative purposes, and are not to be construed as limiting the scope of the invention in any way.

PREPARATION 1

Synthesis of 1-(Methoxycarbonyl)-1,2-dihydropyridine(1A)

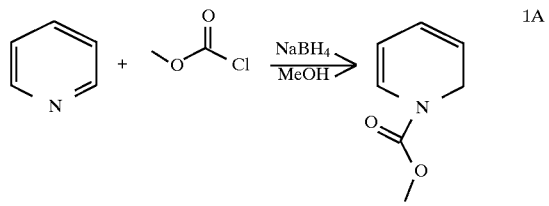

Methyl chloroformate (30.9 mL/400 mmol) was added via syringe to a mixture of pyridine (31.6 g/400 mmol) and sodium borohydride (16.0 g/420 mmol) in methanol (150 mL) at −78° C. Stirred for two hours then poured in to water then extracted with diethyl ether (3×300 mL). The extracts were dried over $NaCl/Na_2SO_4$ then evaporated. The residue was purified by preparative chromatography using silica gel eluting with ethyl acetate/hexanes to yield the 1-(methoxycarbonyl)-1,2-dihydropyridine, 1A (20.2 g/130 mmol).

Synthesis of 2-Aza-2,6-(dimethoxycarbonyl)-bicyclo[2.2.2]oct-7-ene(1B)

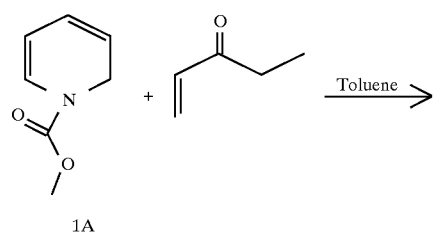

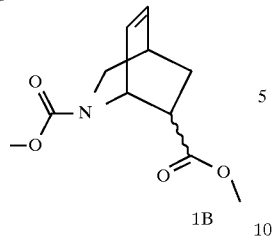

1B

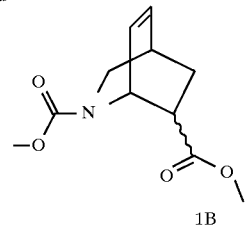

1B

A solution of 1-(methoxycarbonyl)-1,2-dihydropyridine, 1A (18 g/129 mmol) and methyl acrylate (38 mL/646 mmol) in toluene was refluxed for 3 days. Added an additional methyl acrylate (38 mL/646 mmol) and refluxed 24 hours. The reaction was evaporated and the residue was purified by flash chromatography eluting with ethyl acetate to yield 2-aza-2,6-(dimethoxycarbonyl)-bicyclo[2.2.2]oct-7-ene, 1B (5 g).

A solution of 1-(methoxycarbonyl)-1,2-dihydropyridine, 1A (20.2 g/130 mmol) and methyl acrylate (55.9 g/650 mmol) in toluene was refluxed for 3 days. The reaction was evaporated and the residue was purified by flash chromatography eluting with ethyl acetate to yield 2-aza-2,6-(dimethoxycarbonyl)-bicyclo[2.2.2]oct-7-ene, 1B (7.0 g/31.1 mmol).

Synthesis of 2-Aza-2,6-(dimethoxycarbonyl)-bicyclo[2.2.2]octane(1C)

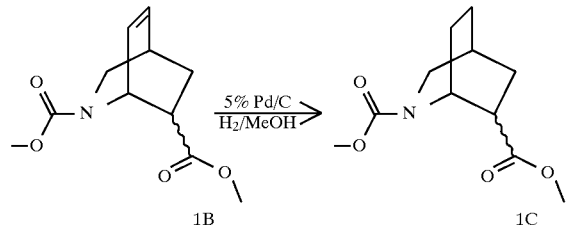

1B    1C

2-Aza-2,6-(dimethoxycarbonyl)-bicyclo[2.2.2]oct-2-ene, 1B, (7.0 g/31.1 mmol) was treated with 5% Pd/C (0.7 g) in MeOH (90 mL) at 60 PSIG of hydrogen at room temperature for five hours. The catalyst was removed by filtration to yield 2-Aza-2,6-(dimethoxycarbonyl)-bicyclo[2.2.2]octane, 1C, (5.5 g/24.2 mmol).

PREPARATION 2

Synthesis of 1-(Methoxycarbonyl)-1,2-dihydropyridine (1A)

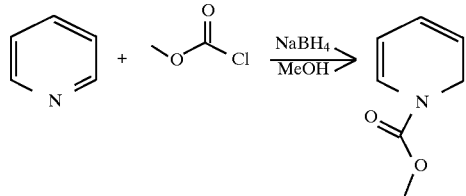

1A

Methyl chloroformate (30.9 mL/400 mmol) was added via syringe to a mixture of pyridine (31.6 g/400 mmol) and sodium borohydride (16.0 g/420 mmol) in methanol (150 mL) at −78° C. Stirred for two hours then poured in to water then extracted with diethyl ether (3×300 mL). The extracts were dried over NaCl/Na₂SO₄ then evaporated. The residue was purified by preparative chromatography using silica gel eluting with ethyl acetate/hexanes to yield the 1-(methoxycarbonyl)-1,2-dihydropyridine, 1A (20.2 g/130 mmol).

EXAMPLE 1

Synthesis of 2-Aza-6-(4-hexyloxy-1,2,5-thiadiaz-3-yl)-2,6-dimethoxycarbonyl)-bicyclo[2.2.2]oct-7-ene (1Dx)

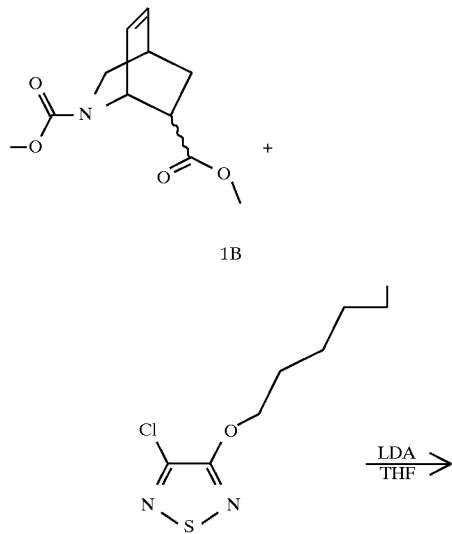

Synthesis of 2-Aza-2,6-(dimethoxycarbonyl)-bicyclo[2.2.2]oct-7-ene(1B)

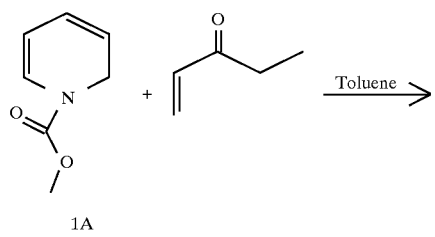

1A

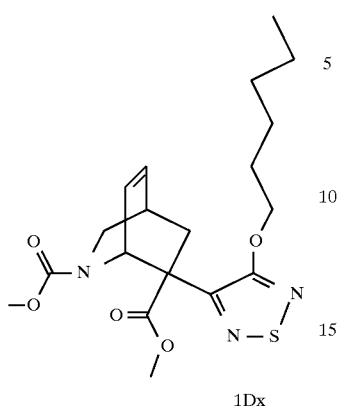

1Dx

Lithium diisopropylamide (24.4 mmol) was added to a solution of 2-aza-2,6-(dimethoxycarbonyl)-bicyclo[2.2.2]oct-7-ene,1B (5.0 g/22.0 mmol) in THF (150 mL) at −78° C. The solution was stirred for 1 hours whereupon 3-chloro-4-hexyloxy-1,2,5-thiadiazole (5.4 g/24.4 mmol) in THF (25 mL) was added dropwise to the solution then stirred for 1 hour at −78° C. then at room temperature for 2 hours. The reaction was quenched with brine then extracted with ethyl acetate. The extracts were dried over NaCl/Na$_2$SO$_4$ then evaporated to yield crude 2-aza-6-(4-butyloxy-1,2,5-thiadiaz-3-yl)-2,6-dimethoxycarbonyl)-bicyclo[2.2.2]oct-7-ene1Dx (9 g).

Synthesis of 2-Aza-6-(4-hexyloxy-1,2,5-thiadiaz-3-yl)-2-(methoxycarbonyl)-bicyclo[2.2.2]oct-7-ne (1Fx)

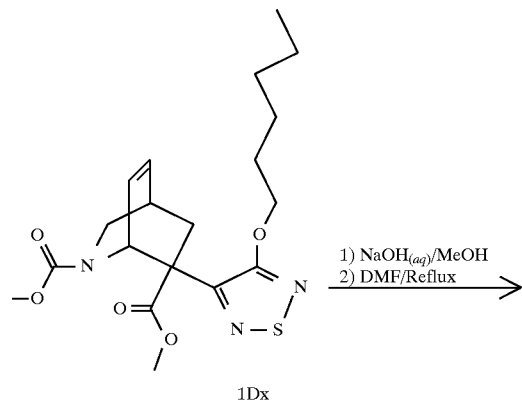

1Dx

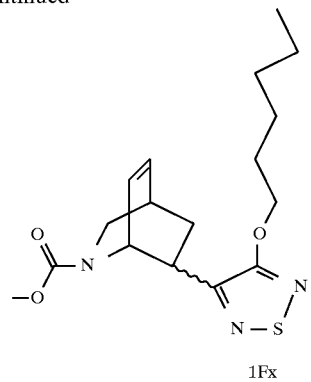

1Fx

A solution of 2-aza-6-(4-hexyloxy-1,2,5-thiadiaz-3-yl)-2,6-dimethoxycarbonyl)-bicyclo[2.2.2]oct-7-ene,1Dx (9 g) in 3N NaOH$_{(aq)}$ (100 mL) and MeOH (200 mL) was refluxed for 16 hours. Methanol was evaporated then the residue was acidified with aqueous HCl then extracted with ethyl acetate. The extracts were evaporated to yield the intermediate acid. A solution of the acid (1.5 g/3.8 mmol) in DMF (10 mL) was refluxed for 5 hours. The reaction was evaporated to yield 2-aza-6-(4-hexyloxy-1,2,5-thiadiaz-3-yl)-2-(methoxycarbonyl)-bicyclo[2.2.2]octane, 1Fx.

Synthesis of 2-Aza-6-(4-hexyloxy-1,2,5-thiadiaz-3-yl)-bicyclo[2.2.2]oct-7-ene(1Gx)

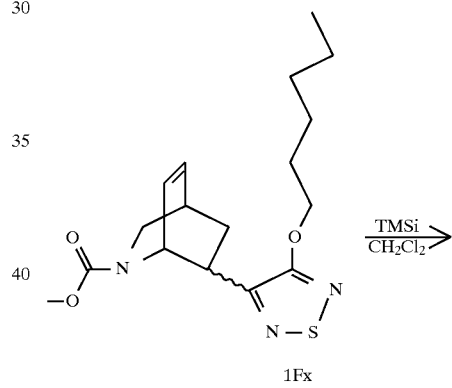

1Fx

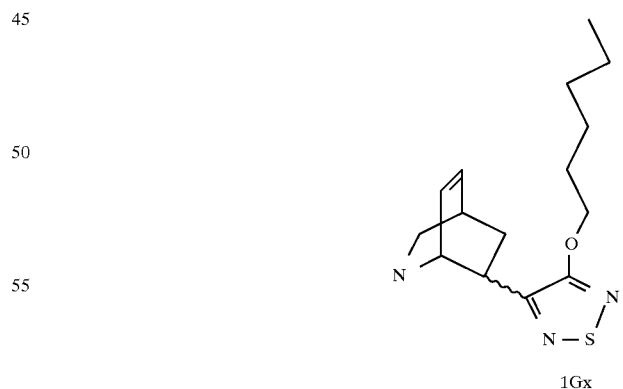

1Gx

A solution of 2-aza-6-(4-hexyloxy-1,2,5-thiadiaz-3-yl)-2-(methoxycarbonyl)-bicyclo[2.2.2]oct-7-ene,1Fx (214 mg/0.6 mmol) and iodotrimethylsilane (0.1 mL.0.73 mmol) in methylene chloride (2 mL) was stirred at room temperature for 4 hours. Saturated NaHCO$_{3(aq)}$ was added to the reaction which was then extracted with methylene chloride (3×10 mL). The extracts were dried over NaCl/Na$_2$SO$_4$ then evaporated to yield of the crude product. The oil was purified by flash chromatography eluting with ammonium hydroxide/ethanol in chloroform to yield 2-aza-6-(4-butyloxy-1,2,5-thiadiaz-3-yl)-bicyclo[2.2.2]oct-7-ene, 1Gx. The mixture of diastereomers of 2-aza-6-(4-hexyloxy-1,2,5-thiadiaz-3-yl)-2-methyl-bicyclo[2.2.2]oct-7-ene, was isolated as the oxalate salt to yield the title compound (Compound 1) (mp=80°–82° C.).

EXAMPLE 2

Synthesis of 2-Aza-6-(4-butyloxy-1,2,5-thiadiaz-3-yl)-2-methyl-bicyclo[2.2.2]oct-7-ene 2-Aza-6-(4-butyloxy-1,2,5-thiadiaz-3-yl)-2-methyl-bicyclo[2.2.2]oct-7-ene (mp=196°–198° C.) was made by the same general procedure as described by Example 1.

EXAMPLE 3

Synthesis of 2-Aza-6-(4-butyloxy-1,2,5-thiadiaz-3-yl)-2,6-dimethoxycarbonyl)-bicyclo[2.2.2]octane (1D)

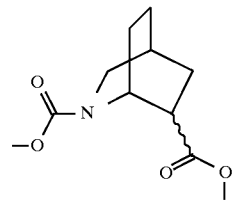

1C

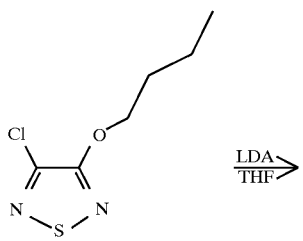

LDA/THF

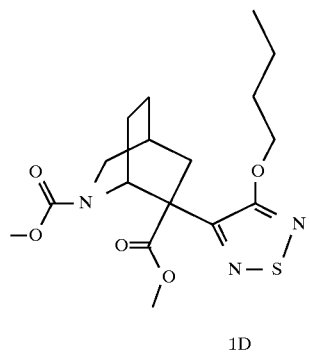

1D

Lithium diisopropylamide (24.2 mmol) was added to a solution of 2-aza-2,6-(dimethoxycarbonyl)-bicyclo[2.2.2]octane1C (5.0 g/22.0 mmol) in THF (100 mL) at −78° C. The solution was stirred for 1.5 hours whereupon 3-chloro-4-butyloxy-1,2,5-thiadiazole (4.7 g/24.2 mmol) in THF (25 mL) was added dropwise to the solution then stirred for 1 hour at −78° C. then at room temperature for 2 hours. The reaction was quenched with water then extracted with ethyl acetate (3×250 mL). The extracts were dried over NaCl/Na$_2$SO$_4$ then evaporated to yield crude 2-aza-6-(4-butyloxy-1,2,5-thiadiaz-3-yl)-2,6-dimethoxycarbonyl)-bicyclo[2.2.2]octane1D (8.4 g).

Synthesis of 2-Aza-6-(4-butyloxy-1,2,5-thiadiaz-3-yl)-2-(methoxycarbonyl)-bicyclo[2.2.2]octane(1F)

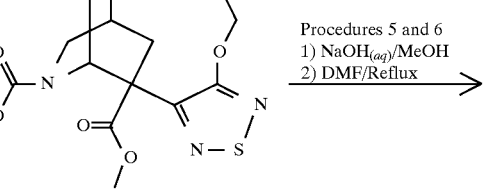

1D

Procedures 5 and 6
1) NaOH$_{(aq)}$/MeOH
2) DMF/Reflux

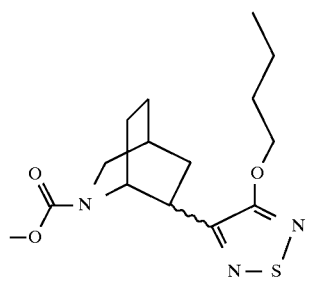

1F

A solution of 2-aza-6-(4-butyloxy-1,2,5-thiadiaz-3-yl)-2,6-dimethoxycarbonyl)-bicyclo[2.2.2]octane1D (8.4 g) in 3N NaOH$_{(aq)}$ (100 mL) and MeOH (200 mL) was refluxed for 5 hours then stirred overnight at room temperature. Methanol was evaporated then the residue was acidified with aqueous HCl then extracted with ethyl acetate (3×100 mL). The extracts were evaporated to yield the intermediate acid. A solution of the acid (6.3 g/17.1 mmol) in DMF (55 mL) was refluxed for 5 hours. The reaction was evaporated to yield 2-aza-6-(4-butyloxy-1,2,5-thiadiaz-3-yl)-2-(methoxycarbonyl)-bicyclo[2.2.2]octane, 1F (5.5 g)

EXAMPLE 4

Synthesis of 2-Aza-6-(4-butyloxy-1,2,5-thiadiaz-3-yl)-bicyclo[2.2.2]octane(1G) and 2-Aza-6-(4-butyloxy-1,2,5-thiadiaz-3-yl)-2-methyl-bicyclo[2.2.2]octane(1H)

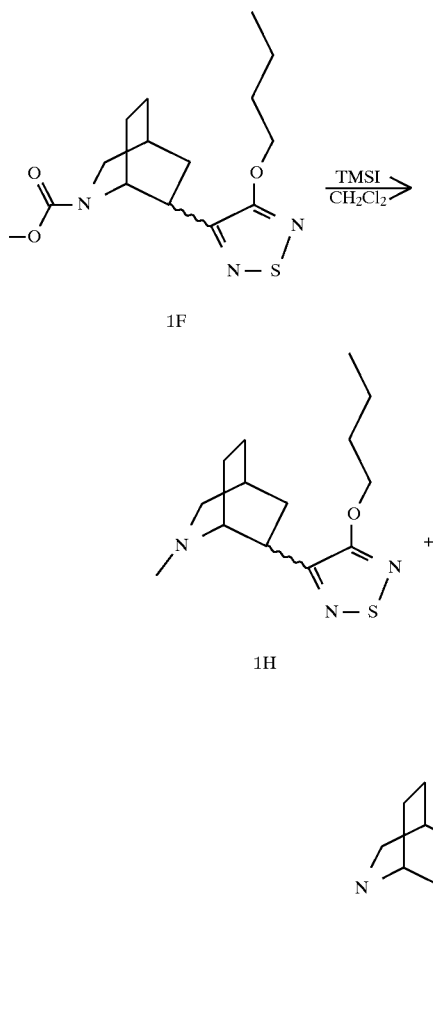

A solution of 2-aza-6-(4-butyloxy-1,2,5-thiadiaz-3-yl)-2-(methoxycarbonyl)-bicyclo[2.2.2]octane, 1F (5.5 g/17.1 mmol) and iodotrimethylsilane (2.9 mL/20.5 mmol) in methylene chloride (35 mL) was stirred at room temperature for 5 hours. Saturated NaHCO$_{3(aq)}$ was added to the reaction which was then extracted with methylene chloride (2×50 mL). The extracts were dried over NaCl/Na$_2$SO$_4$ then evaporated to yield 5.6 g of a crude oil. The oil was purified by flash chromatography eluting with 5% triethylamine in ethyl acetate to yield the ENDO and EXO diastereomers of 2-aza-6-(4-butyloxy-1,2,5-thiadiaz-3-yl)-bicyclo[2.2.2]octane, 1G and 2-aza-6-(4-butyloxy-1,2,5-thiadiaz-3-yl)-2-methyl-bicyclo[2.2.2]octane, 1H. ENDO 2-aza-6-(4-butyloxy-1,2,5-thiadiaz-3-yl)-2-methyl-bicyclo[2.2.2]octane was isolated as the oxalate salt to yield 803 mg Compound 3 (mp=135°–136° C.). ENDO 2-aza-6-(4-butyloxy-1,2,5-thiadiaz-3-yl)-bicyclo[2.2.2]octane was isolated as the oxalate salt to yield 245 mg Compound 4 (mp=118°–120° C.). EXO 2-aza-6-(4-butyloxy-1,2,5-thiadiaz-3-yl)-bicyclo[2.2.2]octane was isolated as the oxalate salt to yield 182 mg Compound 5 (mp=154°–155° C.) EXO 2-aza-6-(4-butyloxy-1,2,5-thiadiaz-3-yl)-2-methyl-bicyclo[2.2.2]octane, was isolated as the oxalate salt to yield 59 mg Compound 6 (mp=147°–149° C.).

Note: The formation of 1H is inhibited by evaporating the reaction after 5 hours then adding saturated NaHCO$_{3(aq)}$ and extracting with ethyl acetate.

EXAMPLE 5

Synthesis of ENDO 2-Aza-6-(4-hexyloxy-1,2,5-thiadiaz-3-yl)-2-methyl-bicyclo[2.2.2]octane, ENDO 2-Aza-6-(4-hexyloxy-1,2,5-thiadiaz-3-yl)-2-methyl-bicyclo[2.2.2]octane (Compound 7) (mp=114°–117° C.) was made using substantially the same general procedure as described by Example 4.

EXAMPLE 6

Synthesis of EXO 2-Aza-6-(4-hexyloxy-1,2,5-thiadiaz-3-yl)-2-methyl-bicyclo[2.2.2]octane, EXO 2-Aza-6-(4-hexyloxy-1,2,5-thiadiaz-3-yl)-2-methyl-bicyclo[2.2.2]octane (Compound 8) (mp=133°–135° C.) was made using substantially the same general procedure as described by Example 4.

EXAMPLE 7

Decarboxylation of 2-Aza-6-(4-butylthio-1,2,5-thiadiaz-3-yl)-2,6-dimethoxycarbonyl)-bicyclo[2.2.2]octane(1I)

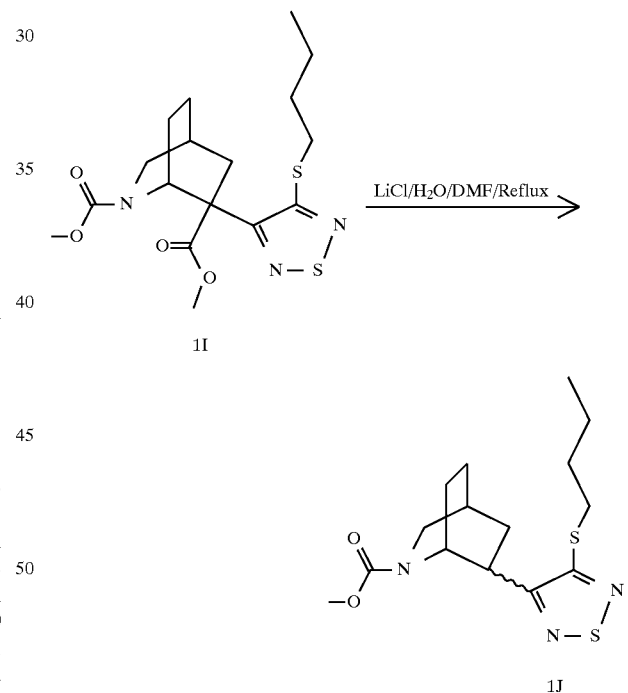

2-Aza-6-(4-thiobutyl-1,2,5-thiadiaz-3-yl)-2,6-dimethoxycarbonyl)-bicyclo[2.2.2]octane (1I) was made by the same general procedure as 2-aza-6-(4-butyloxy-1,2,5-thiadiaz-3-yl)-2,6-dimethoxycarbonyl)-bicyclo[2.2.2]octane (1D).

A mixture of 2-aza-6-(4-thiobutyl-1,2,5-thiadiaz-3-yl)-2,6-dimethoxycarbonyl)-bicyclo[2.2.2]octane, 1I (0.8 g/2.0 mmol), lithium chloride (170 mg/4.0 mmol), water (54 mg/3.0 mmol), and DMF (5 mL) were refluxed for 5 hours. The reaction was poured into water then extracted with ethyl acetate (3×75 mL). The extracts were dried over NaCl/

Na₂SO₄ then evaporated to yield 2-aza-6-(4-butylthio-1,2,5-thiadiaz-3-yl)-2-methoxycarbonyl)-bicyclo[2.2.2]octane, 1J (0.4 g).

Synthesis of 2-Aza-6-(4-butylthio-1,2,5-thiadiaz-3-yl)-bicyclo[2.2.2]octane(1Gy)

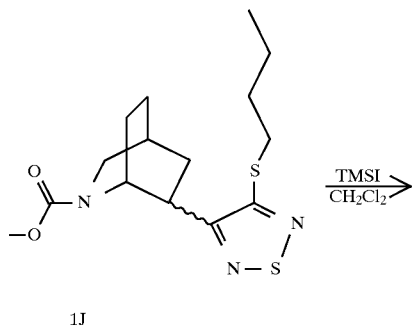

1J

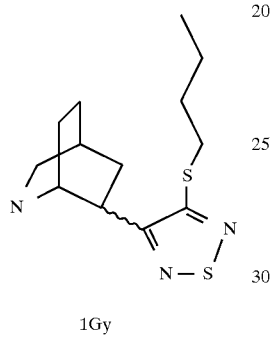

1Gy

A solution of 2-aza-6-(4-thiobutyl-1,2,5-thiadiaz-3-yl)-2-(methoxycarbonyl)-bicyclo[2.2.2]octane,1J (0.1 g/2.9 mmol) and iodotrimethylsilane (0.5 mL/3.4 mmol) in methylene chloride (30 mL) was stirred at room temperature for 7 hours. Concentrated the reaction on a rotary evaporator. Saturated NaHCO₃$_{(aq)}$ was added to the reaction which was then extracted with methylene chloride (3×75 mL). The extracts were dried over NaCl/Na₂SO₄ then evaporated to yield of the crude product. The oil was purified by flash chromatography eluting with ammonium hydroxide/ethanol in chloroform to yield EXO and ENDO 2-aza-6-(4-thiobutyl-1,2,5-thiadiaz-3-yl)-bicyclo[2.2.2]octane, 1Gy, 360 mg and 402 mg respectively. ENDO 2-aza-6-(4-butylthio-1,2,5-thiadiaz-3-yl)-bicyclo[2.2.2]octane was isolated as the oxalate salt to yield Compound 9 (mp=120°–124° C.). EXO 2-aza-6-(4-butylthio-1,2,5-thiadiaz-3-yl)-bicyclo[2.2.2]octane was isolated as the oxalate salt to yield Compound 10 (mp=168°–171° C.).

EXAMPLE 8

Synthesis of ENDO 2-Aza-6-(4-propylthio-1,2,5-thiadiaz-3-yl)-bicyclo[2.2.2]octane ENDO 2-Aza-6-(4-propylthio-1,2,5-thiadiaz-3-yl)-bicyclo[2.2.2]octane (Compound 11), (mp=126°–128° C.) was made using substantially the same general procedure as described by Example 7.

EXAMPLE 9

Synthesis of ENDO 2-Aza-6-(4-propoxy-1,2,5-thiadiaz-3-yl)-bicyclo[2.2.2]octane

ENDO 2-Aza-6-(4-propoxy-1,2,5-thiadiaz-3-yl)-bicyclo [2.2.2]octane, (Compound 12) (mp=170°–172° C.) was made using substantially the same general procedure as described by Example 7.

EXAMPLE 10

Synthesis of EXO 2-Aza-6-(4-propoxy-1,2,5-thiadiaz-3-yl)-bicyclo[2.2.2]octane

EXO 2-Aza-6-(4-propoxy-1,2,5-thiadiaz-3-yl)-bicyclo [2.2.2]octane, (Compound 13) (mp=157°–158° C.) was made using substantially the same general procedure as described by Example 7.

EXAMPLE 11

Synthesis of EXO 2-Aza-6-(4-methylthio-1,2,5-thiadiaz-3-yl)-bicyclo[2.2.2]octane EXO 2-Aza-6-(4-methylthio-1,2,5-thiadiaz-3-yl)-bicyclo [2.2.2]octane, (Compound 14) (mp=208°–211° C.) was made using substantially the same general procedure as described by Example 7.

EXAMPLE 12

Synthesis of 2-aza-6-(4-propanesulfonyl-1,2,5-thiadiaz-3-yl)-2-methoxycarbonyl)-bicyclo[2.2.2]octane

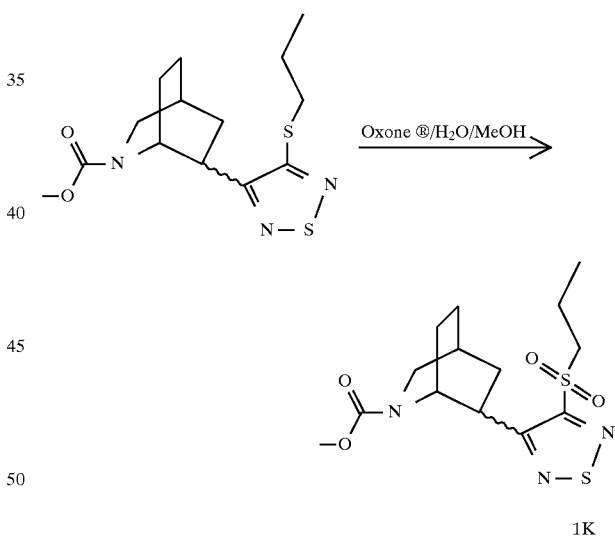

1K

A solution of 2-Aza-6-(4-thiopropyl-1,2,5-thiadiaz-3-yl)-bicyclo[2.2.2]octane, as a mixture of ENDO and EXO isomers, (3.4 g/10.4 mmol) in methanol (10 mL), water(25 mL), and 1N HCl$_{(aq)}$ (10 mL) was cooled in an ice bath. Oxone® (9.6 g/15.6 mmol) in water (50 mL) was added dropwise to the reaction. The reaction was allowed to stir overnight at room temperature. The reaction was evaporated then taken up in saturated NaHCO₃$_{(aq)}$ and extracted with chloroform (3×100 mL). The extracts were dried over NaCl/Na₂SO₄ then evaporated to yield the 2-Aza-6-(4-propanesulfonyl-1,2,5-thiadiaz-3-yl)-bicyclo[2.2.2] octane,1K (3.6 g).

Synthesis of 2-aza-6-(4-pentylthio-1,2,5-thiadiaz-3-yl)-2-methoxycarbonyl)-bicyclo[2.2.2]octane

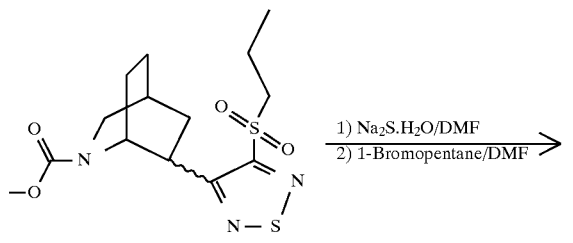

1K

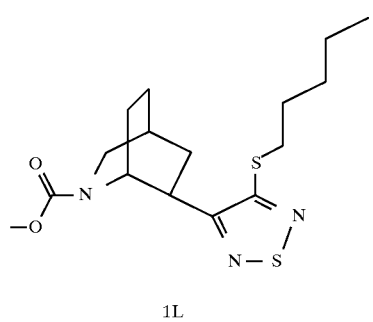

1L

Sodium sulfide nonahydrate (0.5 g/2.0 mmol) was added to a solution of 2-aza-6-(4-propanesulfonyl-1,2,5-thiadiaz-3-yl)-bicyclo[2.2.2]octane, 1K (0.7 g/2.0 mmol) in DMF (8 mL) at 100° C. The reaction was stirred for 3 hours whereupon 1-bromopentane (0.3 mL/2.0 mmol) in DMF (2 mL) was added to the reaction. Stirred at 100° C. for 1 hour then overnight at room temperature. Poured the reaction into water then extracted with ethyl acetate (3×50 mL). The extracts were dried over NaCl/Na$_2$SO$_4$ then evaporated to yield 0.8 g of an oil. Purified by flash chromatography eluting with 25% ethyl acetate in hexanes to yield a mixture of ENDO and EXO 2-aza-6-(4-pentylthio-1,2,5-thiadiaz-3-yl)-2-methoxycarbonyl)-bicyclo[2.2.2]octane, 1L (309 mg).

Synthesis of 2-Aza-6-(4-pentylthio-1,2,5-thiadiaz-3-yl)-bicyclo[2.2.2]octane(1Gz)

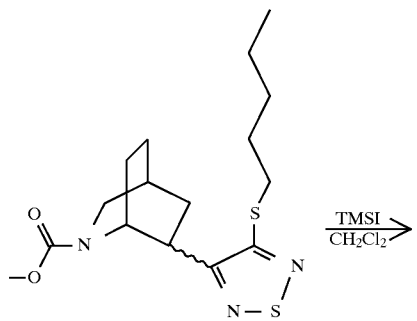

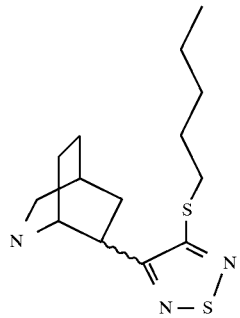

A solution of 2-aza-6-(4-pentylthio-1,2,5-thiadiaz-3-yl)-2-(methoxycarbonyl)-bicyclo[2.2.2]octane,1L (300 mg/0.9 mmol) and iodotrimethylsilane (0.2 mL/1.0 mmol) in methylene chloride (5 mL) was stirred at room temperature for 7 hours. Concentrated the reaction on a rotary evaporator. Saturated NaHCO$_{3(aq)}$ was added to the reaction which was then extracted with methylene chloride (3×25 mL). The extracts were dried over NaCl/Na$_2$SO$_4$ then evaporated to yield of the crude product. The oil was purified by flash chromatography eluting with triethylamine in ethyl acetate to yield EXO and ENDO 2-aza-6-(4-pentylthio-1,2,5-thiadiaz-3-yl)-bicyclo[2.2.2]octane, 1Gz, 38 mg and 62 mg respectively. ENDO 2-aza-6-(4-thiopentyl-1,2,5-thiadiaz-3-yl)-bicyclo[2.2.2]octane was isolated as the oxalate salt to yield Compound 15 (mp=88°–89° C.). EXO 2-aza-6-(4-pentylthio-1,2,5-thiadiaz-3-yl)-bicyclo[2.2.2]octane was isolated as the oxalate salt to yield Compound 16 (mp=138°–141° C.).

EXAMPLE 13

The following compounds were prepared using substantially the method described by Example 12:

EXO 2-Aza-6-(4-((4-methylpentyl)thio)-1,2,5-thiadiaz-3-yl)-bicyclo[2.2.2]octane, (Compound 17) (mp=157°–158° C.);

ENDO 2-Aza-6-(4-((4-methylpentyl)thio)-1,2,5-thiadiaz-3-yl)-bicyclo[2.2.2]octane, (Compound 18) (mp=87°–90° C.);

ENDO 2-Aza-6-(4-methylthio)-1,2,5-thiadiaz-3-yl)-bicyclo[2.2.2]octane, (Compound 19) (mp=184°–185° C.);

ENDO 2-Aza-6-(4-((4,4,4-trifluorobutyl)thio)-1,2,5-thiadiaz-3-yl)-bicyclo[2.2.2]octane, (Compound 20) (mp=151°–153° C.);

2-Aza-6-(4-(((4-trifluoromethyl)phenyl)methylthio)-1,2,5-thiadiaz-3-yl)-bicyclo[2.2.2]octane, (Compound 21) (mp=67°–75° C.);

EXO 2-Aza-6-(4-(((4-trifluoromethyl)phenyl)methylthio)-1,2,5-thiadiaz-3-yl)-bicyclo[2.2.2]octane, (Compound 22) (mp=175°–177° C.);

ENDO 2-Aza-6-(4-((4-cyanophenyl)methylthio)-1,2,5-thiadiaz-3-yl)-bicyclo[2.2.2]octane, (Compound 23) (mp=68°–74° C.);

EXO 2-Aza-6-(4-((4-cyanophenyl)methylthio)-1,2,5-thiadiaz-3-yl)-bicyclo[2.2.2]octane, (Compound 24) (mp=187°–188° C.);

ENDO 2-Aza-6-(4-((5-cyanothien-2-yl)methylthio)-1,2,5-thiadiaz-3-yl)-bicyclo[2.2.2]octane, (Compound 25) (mp=65°–69° C.);

EXO 2-Aza-6-(4-((5-cyanothien-2-yl)methylthio)-1,2,5-thiadiaz-3-yl)-bicyclo[2.2.2]octane, (Compound 26) (mp=155°–158° C.);

EXO 2-Aza-6-(4-hexylthio-1,2,5-thiadiaz-3-yl)-bicyclo[2.2.2]octane, (Compound 27) (mp=88°–90° C.);

EXO 2-Aza-6-(4-hexylthio-1,2,5-thiadiaz-3-yl)-bicyclo[2.2.2]octane, (Compound 28) (mp=142°–144° C.);

EXO 2-Aza-6-(4-(3-thienylpropylthio)-1,2,5-thiadiaz-3-yl)-bicyclo[2.2.2]octane, (Compound 29) (mp=124°–126° C.);

EXAMPLE 14

Synthesis of 2-aza-6-(4-pentoxy-1,2,5-thiadiaz-3-yl)-2-methoxycarbonyl)-bicyclo[2.2.2]octane

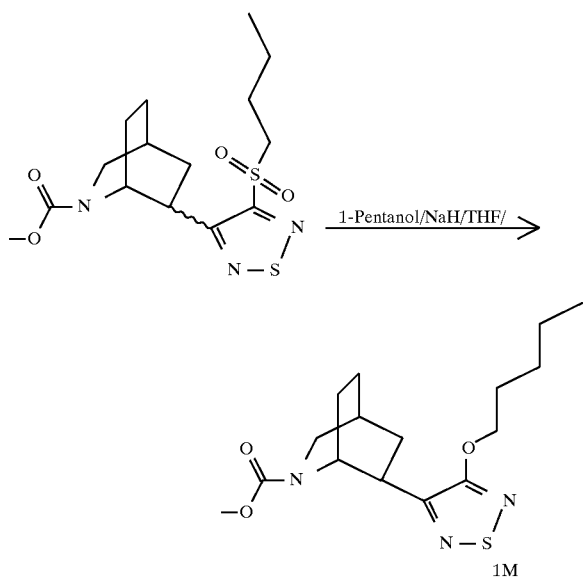

Sodium hydride (8.4 mmol) was added to a solution of 1-pentanol (1.2 g/14 mmol) in THF (20 mL). Refluxed the reaction for 2 hours then 2-aza-6-(4-propanesulfonyl-1,2,5-thiadiaz-3-yl)-bicyclo[2.2.2]octane (2.8 mmol) in THF (5 mL) was added to the alkoxide. Reflux was continued overnight. The reaction was quenched with saturated NaCl (aq) then extracted with ethyl acetate (3×75 mL). The organic extracts were dried over MgSO$_4$ then evaporated to yield 1.1 g of an oil. The oil was purified by radial chromatography eluting with 20% ethyl acetate in hexanes to yield 2-aza-6-(4-pentoxy-1,2,5-thiadiaz-3-yl)-2-methoxycarbonyl)-bicyclo[2.2.2]octane (600 mg/1.7 mmol).

Synthesis of 2-Aza-6-(4-pentoxy-1,2,5-thiadiaz-3-yl)-bicyclo[2.2.2]octane(1Ga)

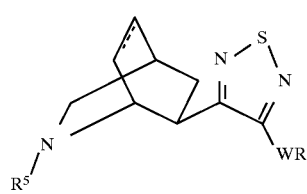

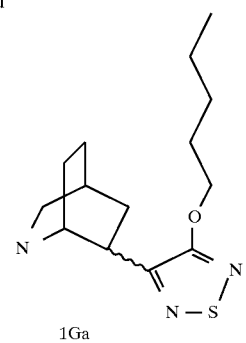

A solution of 2-aza-6-(4-pentoxy-1,2,5-thiadiaz-3-yl)-2-(methoxycarbonyl)-bicyclo[2.2.2]octane,1M (0.47 g/1.3 mmol) and iodotrimethylsilane (0.22 mL/1.6 mmol) in methylene chloride (15 mL) was stirred at room temperature for 7 hours. Concentrated the reaction on a rotary evaporator. Saturated NaHCO$_{3(aq)}$ was added to the reaction which was then extracted with methylene chloride (3×25 mL). The extracts were dried over NaCl/Na$_2$SO$_4$ then evaporated to yield of the crude product. The oil was purified by flash chromatography eluting with triethylamine in ethyl acetate to yield EXO and ENDO 2-aza-6-(4-pentoxy-1,2,5-thiadiaz-3-yl)-bicyclo[2.2.2]octane, 1Ga, 82 mg and 122 mg respectively. ENDO 2-aza-6-(4-pentoxy-1,2,5-thiadiaz-3-yl)-bicyclo[2.2.2]octane was isolated as the oxalate salt to yield Compound 30 (mp126°–27° C.). EXO 2-aza-6-(4-pentoxy-1,2,5-thiadiaz-3-yl)-bicyclo[2.2.2]octane was isolated as the oxalate salt to yield Compound 31 (mp=124°–130° C.).

EXAMPLE 15

Synthesis of ENDO 2-Aza-6-(4-((4-trifluoromethylphenyl)methoxy)-1,2,5-thiadiaz-3-yl)-bicyclo[2.2.2]octane EXO 2-Aza-6-(4-((4-trifluoromethylphenyl)methoxy)-1,2,5-thiadiaz-3-yl)-bicyclo[2.2.2]octane, (Compound 32) (mp=187°–190° C.) was made using substantially the same general procedure as described by Example 14.

EXAMPLE 16

Synthesis of EXO 2-Aza-6-(4-((4-trifluoromethylphenyl)methoxy)-1,2,5-thiadiaz-3-yl)-bicyclo[2.2.2]octane EXO 2-Aza-6-(4-((4-trifluoromethylphenyl)methoxy)-1,2,5-thiadiaz-3-yl)-bicyclo[2.2.2]octane, (Compound 33) (mp=224°–225° C.) was made using substantially the same general procedure as described by Example 14.

We claim:

1. A compound of Formula I wherein

W is oxygen or sulphur;

R is selected from the group consisting of hydrogen, R$^4$, G,

C$_{3-10}$-cycloalkyl, C$_{4-12}$-(cycloalkylalkyl), aryl, aryl (C$_1$–C$_3$)-alkyl, C$_1$–C$_6$ alkylheterocycle and heterocycle, each of which is optionally substituted with one or more independently selected from the group consisting of halogen(s), —CF$_3$, —CN, C$_{1-15}$-alkyl, C$_{2-5}$-alkenyl, C$_{2-5}$-alkynyl, and C$_{1-10}$-alkoxy;

R$^5$ is hydrogen, R$^4$, G, C$_{3-10}$-cycloalkyl, C$_{4-12}$-(cycloalkylalkyl), aryl, each of which is optionally substituted with one or more independently selected from the group consisting of halogen(s), —CF$_3$, —CN, C$_{1-15}$-alkyl, C$_{2-5}$-alkenyl, C$_{2-5}$-alkynyl, and C$_{1-10}$-alkoxy;

R$^4$ is selected from the group consisting of C$_{1-15}$-alkyl, substituted C$_{1-15}$-alkyl, C$_{2-15}$-alkenyl, and C$_{2-15}$-alkynyl;

G is selected from one of the following azacyclic or azabicyclic ring systems:

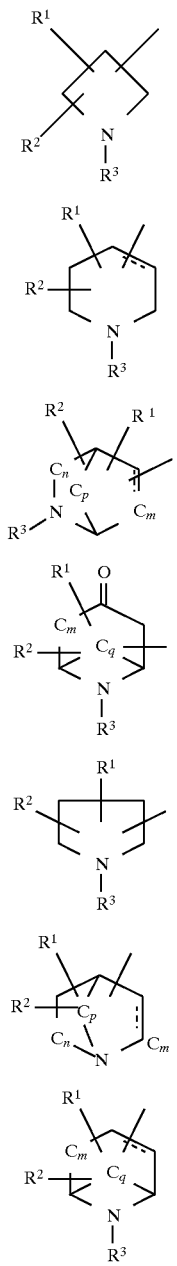

or G can optionally be substituted C$_3$–C$_8$ cycloalkyl or optionally substituted C$_{1-6}$-alkyl wherein the substitution is —NR$^6$R$^7$;

R$^6$ and R$^7$ independently are hydrogen, C$_{1-6}$-alkyl; or R$^6$ and R$^7$ together with the nitrogen atom optionally form a 4- to 6-member ring;

R$^1$ and R$^2$ independently are hydrogen, C$_{1-15}$-alkyl, C$_{2-5}$-alkenyl, C$_{2-5}$-alkynyl, C$_{1-10}$-alkoxy, C$_{1-5}$-alkyl substituted with —OH, —COR$^{6'}$, CH$_2$—OH, halogen, —NH$_2$, carboxy, or phenyl;

R$^3$ is hydrogen, C$_{1-5}$-alkyl, C$_{2-5}$-alkenyl or C$_{2-5}$-alkynyl;

R$^{6'}$ is hydrogen, C$_{1-6}$-alkyl;

n is 0, 1 or 2;

m is 0, 1 or 2;

p is 0, 1 or 2;

q is 1 or 2;

r is 0, 1 or 2;

······ is a single or double bond; or a pharmaceutically acceptable salt or solvate thereof.

2. A compound of claim 1 wherein W is S.

3. A compound of claim 1 wherein W is O; R$^5$ is hydrogen.

4. A compound of claim 1 wherein R is aryl(C$_1$–C$_3$)alkyl.

5. A compound of claim 3 wherein R is selected from benzyl or substituted benzyl.

6. A compound of claim 1 wherein R is thiophene-methyl or substituted thiophene methyl.

7. A compound of claim 1 wherein G is selected from the group consisting of:

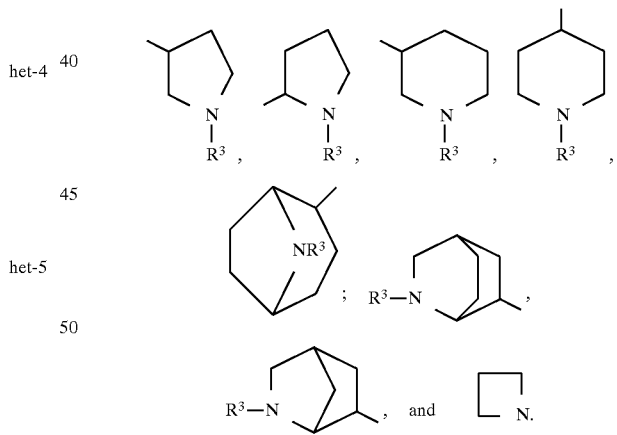

8. A compound of claim 1 wherein R is R$^4$; R$^4$ is substituted C$_1$–C$_3$ alkyl wherein the alkyl is substituted with from one to four substituents independently selected from the group consisting of hydrogen, C$_1$–C$_6$ alkyl, halogen, halogen(C$_1$–C$_6$)alkyl, halogen(C$_2$–C$_6$)alkenyl, C$_2$–C$_6$ alkenyl, (C$_1$–C$_6$ alkyl) amino, aryl, substituted aryl, —SR$^{20}$, and OR$^{20}$; wherein R$^{20}$ is selected from the group consisting of C$_{1-15}$-alkyl, C$_{2-15}$-alkenyl, C$_{2-15}$-alkynyl, aryl, and substituted aryl.

9. A compound of claim 8 wherein R is R$^4$; R$^4$ is substituted C$_1$–C$_3$ alkyl substituted with a substituent selected from the group consisting of hydrogen, C$_1$–C$_6$ alkyl, halogen, halogen($C_1$–$C_6$)alkyl, halogen($C_2$–$C_6$) alkenyl, $C_2$–$C_6$ alkenyl, —$SR^{20}$; and $OR^{20}$; wherein $R^{20}$ is selected from the group consisting of $C_{1-15}$-alkyl, $C_{2-15}$-alkenyl, and $C_{2-5}$-alkynyl.

10. A compound of claim 1 wherein the compound is selected from the group consisting of:

2-Aza-6-(4-hexyloxy-1,2,5-thiadiaz-3-yl)-2,6-dimethoxycarbonyl)-bicyclo[2.2.2]oct-7-ene;

2-Aza-6-(4-butyloxy-1,2,5-thiadiaz-3-yl)-2-methyl-bicyclo[2.2.2]oct-7-ene;

2-Aza-6-(4-butyloxy-1,2,5-thiadiaz-3-yl)-2,6-dimethoxycarbonyl)-bicyclo[2.2.2]octane;

2-Aza-6-(4-butyloxy-1,2,5-thiadiaz-3-yl)-bicyclo[2.2.2]octane;

2-Aza-6-(4-butyloxy-1,2,5-thiadiaz-3-yl)-2-methyl-bicyclo[2.2.2]octane;

ENDO 2-Aza-6-(4-hexyloxy-1,2,5-thiadiaz-3-yl)-2-methyl-bicyclo[2.2.2]octane;

EXO 2-Aza-6-(4-hexyloxy-1,2,5-thiadiaz-3-yl)-2-methyl-bicyclo[2.2.2]octane;

EXO 2-aza-6-(4-butylthio-1,2,5-thiadiaz-3-yl)-bicyclo[2.2.2]octane;

ENDO 2-Aza-6-(4-propylthio-1,2,5-thiadiaz-3-yl)-bicyclo[2.2.2]octane;

ENDO 2-Aza-6-(4-propoxy-1,2,5-thiadiaz-3-yl)-bicyclo[2.2.2]octane;

EXO 2-Aza-6-(4-propoxy-1,2,5-thiadiaz-3-yl)-bicyclo[2.2.2]octane;

EXO 2-Aza-6-(4-methylthio-1,2,5-thiadiaz-3-yl)-bicyclo[2.2.2]octane;

2-aza-6-(4-propanesulfonyl-1,2,5-thiadiaz-3-yl)-2-methoxycarbonyl)-bicyclo[2.2.2]octane;

EXO 2-Aza-6-(4-((4-methylpentyl)thio)-1,2,5-thiadiaz-3-yl)-bicyclo[2.2.2]octane;

ENDO 2-Aza-6-(4-((4-methylpentyl)thio)-1,2,5-thiadiaz-3-yl)-bicyclo[2.2.2]octane;

ENDO 2-Aza-6-(4-methylthio)-1,2,5-thiadiaz-3-yl)-bicyclo[2.2.2]octane;

ENDO 2-Aza-6-(4-((4,4,4-trifluorobutyl)thio)-1,2,5-thiadiaz-3-yl)-bicyclo[2.2.2]octane;

2-Aza-6-(4-(((4-trifluoromethyl)phenyl)methylthio)-1,2,5-thiadiaz-3-yl)-bicyclo[2.2.2]octane;

EXO 2-Aza-6-(4-(((4-trifluoromethyl)phenyl)methylthio)-1,2,5-thiadiaz-3-yl)-bicyclo[2.2.2]octane;

ENDO 2-Aza-6-(4-((4-cyanophenyl)methylthio)-1,2,5-thiadiaz-3-yl)-bicyclo[2.2.2]octane;

EXO 2-Aza-6-(4-((4-cyanophenyl)methylthio)-1,2,5-thiadiaz-3-yl)-bicyclo[2.2.2]octane;

ENDO 2-Aza-6-(4-((5-cyanothien-2-yl)methylthio)-1,2,5-thiadiaz-3-yl)-bicyclo[2.2.2]octane;

EXO 2-Aza-6-(4-((5-cyanothien-2-yl)methylthio)-1,2,5-thiadiaz-3-yl)-bicyclo[2.2.2]octane;

EXO 2-Aza-6-(4-hexylthio-1,2,5-thiadiaz-3-yl)-bicyclo[2.2.2]octane;

EXO 2-Aza-6-(4-hexylthio-1,2,5-thiadiaz-3-yl)-bicyclo[2.2.2]octane;

EXO 2-Aza-6-(4-(3-thienylpropylthio)-1,2,5-thiadiaz-3-yl)-bicyclo[2.2.2]octane;

2-aza-6-(4-pentoxy-1,2,5-thiadiaz-3-yl)-2-methoxycarbonyl)-bicyclo[2.2.2]octane;

ENDO 2-Aza-6-(4-((4-trifluoromethylphenyl)methoxy)-1,2,5-thiadiaz-3-yl)-bicyclo[2.2.2]octane;

EXO 2-Aza-6-(4-((4-trifluoromethylphenyl)methoxy)-1,2,5-thiadiaz-3-yl)-bicyclo[2.2.2]octane;

EXO 2-Aza-6-(4-((4-trifluoromethylphenyl)methoxy)-1,2,5-thiadiaz-3-yl)-bicyclo[2.2.2]octane; or a pharmaceutically acceptable salt or solvate thereof.

11. A pharmaceutical formulation comprising a compound of Formula I together with one or more pharmaceutically acceptable carriers or diluents.

12. A pharmaceutical formulation of claim 11 wherein the formulation is in the form of an oral dosage unit or parenteral dosage unit.

13. A pharmaceutical formulation according to claim 12, wherein said dosage unit comprises from about 0.1 to about 100 mg of a compound of claim 1 together with one or more pharmaceutically acceptable carriers or diluents.

14. A method of treating a disease in the central nervous system caused by malfunctioning of the muscarinic cholinergic system comprising administering to a subject in need thereof a pharmaceutically effective amount of a compound of claim 1.

15. A method for treating a condition associated with the modulation of a muscarinic cholinergic receptor comprising administering to a subject in need thereof a pharmaceutically effective amount of a compound of claim 1.

16. A method for interacting with a muscarinic cholinergic receptor comprising adminstering an effective amount of a compound of claim 1.

* * * * *

UNITED STATES PATENT AND TRADEMARK OFFICE
CERTIFICATE OF CORRECTION

PATENT NO. : 5,834,458

DATED : November 10, 1998

INVENTOR(S) : Charles H. Mitch

It is certified that an error appears in the above-identified patent and that said Letters Patent is hereby corrected as shown below:

In column 30, line 51, please delete 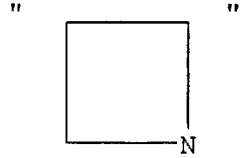

and insert therefor 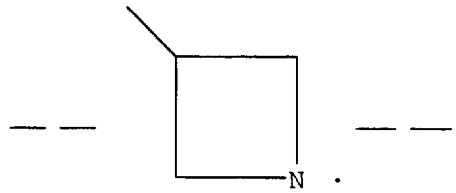

Signed and Sealed this

Twenty-third Day of May, 2000

*Attest:*

Q. TODD DICKINSON

*Attesting Officer*     Director of Patents and Trademarks